(12) United States Patent
Chisholm et al.

(10) Patent No.: US 7,271,283 B2
(45) Date of Patent: Sep. 18, 2007

(54) HIGH REFRACTIVE INDEX, UV-CURABLE MONOMERS AND COATING COMPOSITIONS PREPARED THEREFROM

(75) Inventors: Bret Ja Chisholm, Clifton Park, NY (US); Paul Michael Smigelski, Jr., Schenectady, NY (US); James Edward Pickett, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 281 days.

(21) Appl. No.: 10/897,364

(22) Filed: Jul. 21, 2004

(65) Prior Publication Data

US 2005/0049376 A1    Mar. 3, 2005

(51) Int. Cl.
C07C 323/00 (2006.01)
C07C 321/00 (2006.01)

(52) U.S. Cl. ............ 560/152; 560/121; 560/125; 560/15; 560/17

(58) Field of Classification Search .......... 560/152, 560/15, 16, 17, 121, 125
See application file for complete search history.

(56) References Cited

U.S. PATENT DOCUMENTS

| | | |
|---|---|---|
| 3,227,053 A | 1/1966 | Spalding |
| 3,824,293 A | 7/1974 | Brode |
| 4,059,618 A | 11/1977 | Blumenfeld et al. |
| 4,198,465 A | 4/1980 | Moore et al. |
| 4,362,887 A * | 12/1982 | Kline ............ 560/152 |
| 4,370,434 A | 1/1983 | Kline |
| 4,420,527 A | 12/1983 | Conley |
| 4,576,850 A | 3/1986 | Martens |
| 4,578,445 A | 3/1986 | Sakagami et al. |
| 4,582,885 A | 4/1986 | Barber |
| 4,668,558 A | 5/1987 | Barber |
| 4,710,557 A | 12/1987 | Warren |
| 4,721,377 A | 1/1988 | Fukuda et al. |
| 4,970,135 A | 11/1990 | Kushi et al. |
| 5,175,030 A | 12/1992 | Lu et al. |
| 5,183,597 A | 2/1993 | Lu |
| 5,239,026 A | 8/1993 | Babirad et al. |
| 5,284,736 A | 2/1994 | Kushi et al. |
| 5,395,900 A | 3/1995 | Liaw et al. |
| 5,424,339 A | 6/1995 | Zanka et al. |
| 5,450,235 A | 9/1995 | Smith et al. |
| 5,470,892 A | 11/1995 | Gupta et al. |
| 5,479,555 A | 12/1995 | Rot et al. |
| 5,518,789 A | 5/1996 | Burns et al. |
| 5,626,800 A | 5/1997 | Williams et al. |
| 5,635,278 A | 6/1997 | Williams |
| 5,691,846 A | 11/1997 | Benson, Jr. et al. |
| 5,714,218 A | 2/1998 | Nishio et al. |
| 5,716,681 A | 2/1998 | Williams |
| 5,855,983 A | 1/1999 | Williams |
| 5,883,607 A | 3/1999 | Williams |
| 5,891,931 A | 4/1999 | Leboeuf |
| 5,900,287 A | 5/1999 | Williams |
| 5,908,874 A | 6/1999 | Fong et al. |
| 5,932,626 A | 8/1999 | Fong et al. |
| 5,969,867 A | 10/1999 | Fukushima et al. |
| 5,981,113 A | 11/1999 | Christian |
| 5,988,820 A | 11/1999 | Huang et al. |
| 6,005,137 A | 12/1999 | Moore et al. |
| 6,051,733 A | 4/2000 | Weissman |
| 6,107,364 A | 8/2000 | Fong et al. |
| 6,114,010 A | 9/2000 | Williams |
| 6,130,346 A * | 10/2000 | Nobori et al. ............ 558/51 |
| 6,206,550 B1 | 3/2001 | Fukushima et al. |
| 6,218,074 B1 | 4/2001 | Dueber et al. |
| 6,228,500 B1 | 5/2001 | Hiroshige et al. |
| 6,232,359 B1 | 5/2001 | Christian |
| 6,239,485 B1 | 5/2001 | Peters et al. |
| 6,280,063 B1 | 8/2001 | Fong et al. |
| 6,310,161 B1 | 10/2001 | Weissman |
| 6,313,187 B2 | 11/2001 | LeBoeuf et al. |
| 6,313,245 B1 | 11/2001 | Moore et al. |
| 6,350,035 B1 | 2/2002 | Smith et al. |
| 6,355,754 B1 | 3/2002 | Olson et al. |
| 6,368,682 B1 | 4/2002 | Fong |
| 6,428,889 B1 | 8/2002 | Nagaoka |
| 6,503,564 B1 | 1/2003 | Fleming et al. |
| 6,833,391 B1 | 12/2004 | Chisholm et al. |
| 2001/0025086 A1 | 9/2001 | LeBoeuf et al. |
| 2002/0123589 A1 | 9/2002 | Olson et al. |
| 2002/0126382 A1 | 9/2002 | Smith et al. |

(Continued)

FOREIGN PATENT DOCUMENTS

EP    0 247 861    12/1987

(Continued)

OTHER PUBLICATIONS

STN (ACS) results from UPSTO structure search done Nov. 1, 2006, pp. 40-46.*

(Continued)

*Primary Examiner*—Sanza L. McClendon
(74) *Attorney, Agent, or Firm*—Andrew J. Caruso; William E. Powell, III

(57) ABSTRACT

Disclosed herein are high refractive index monomers that are curable by ultraviolet light. These monomers may be a component of curable compositions useful in the preparation of optical articles. Also disclosed is a method of synthesizing the monomers.

11 Claims, 2 Drawing Sheets

U.S. PATENT DOCUMENTS

| | | |
|---|---|---|
| 2002/0132928 A1 | 9/2002 | Soane et al. |
| 2002/0192459 A1 | 12/2002 | Bacon, Jr. |
| 2003/0224250 A1 | 12/2003 | Setthachayanon et al. |
| 2005/0259303 A1* | 11/2005 | Setthacayanon et al. ...... 359/15 |

FOREIGN PATENT DOCUMENTS

| | | |
|---|---|---|
| EP | 0 406 590 | 1/1991 |
| EP | 0 430 722 | 6/1991 |
| EP | 0 708 164 | 4/1996 |
| EP | 0 759 448 | 2/1997 |
| EP | 1 014 133 | 6/2000 |
| EP | 0 759448 | 1/2002 |
| JP | 62-79210 | * 11/1987 |
| JP | 2-247212 | 10/1990 |
| JP | 2-258819 | 10/1990 |
| JP | 03-153715 | 1/1991 |
| JP | 2002-97217 | 1/1991 |
| JP | 04285654 | 10/1992 |
| JP | 05287040 | 11/1993 |
| JP | 059136310 | 8/1994 |
| JP | 2000009901 | 1/2000 |
| JP | 2001-172253 | 6/2001 |
| WO | WO98/50805 | 11/1998 |
| WO | WO 01/30933 | 5/2001 |
| WO | WO 02/051892 | 7/2002 |
| WO | WO 03/076528 | 9/2003 |

OTHER PUBLICATIONS

Kassem et al. Synthesis of New benzothiazole-2-acrylic acid derivatives. Pakistan Journal Science and Industrial Research, 38 (11-12), 1985, 424-427.*

RJM Zwiers et al., *"Replication of High Precision Aspherical Lenses Using UV-Curable Coatings"*, Conference Location: Limburg, Netherlands, Source Publisherd by: Elsevier Applied Science Publ, London, England and New York, NY USA, pp. 673-677, 1986.

W. Lenore Carman Rasmussen, *"Novel Carbazole Based Methacrylates, Acrylates, and Dimethacrylates To Produce High Refractive Index Polymers"*, Dissertation to Virginia Polytechnic Institute and State University, pp. 1-172, Sep. 26, 2001.

LL Beecroft et al., *High Refractive Index Polymers for Optical Applications*, J.M.S. Pure Appl. Chem., A34(4), pp. 573-586, 1997.

* cited by examiner

HIGH REFRACTIVE INDEX, UV-CURABLE MONOMERS AND COATING COMPOSITIONS PREPARED THEREFROM

BACKGROUND OF INVENTION

Disclosed herein are high refractive index monomers and curable coating compositions prepared from such monomers. The compositions and monomers are suitable for optical articles and particularly for light management films. Also disclosed herein is a method of preparing high refractive index monomers.

In backlight computer displays or other display systems, optical films are commonly used to direct light. For example, in backlight displays, light management films use prismatic structures (often referred to as microstructure) to direct light along a viewing axis (i.e., an axis substantially normal to the display). Directing the light enhances the brightness of the display viewed by a user and allows the system to consume less power in creating a desired level of on-axis illumination. Films for turning or directing light can also be used in a wide range of other optical designs, such as for projection displays, traffic signals, and illuminated signs.

Compositions used to form light management films to direct light desirably have the ability to replicate the microstructure needed to provide the light directing capability upon cure. It is furthermore desirable for the glass transition temperature (Tg) of the cured composition to be high enough for shape retention during storage and use. It is also desirable for light management films made from the cured composition to exhibit high brightness. Finally, the composition used to make light management films advantageously provides a cured composition having a high refractive index. While a variety of materials are presently available for use in light management films, there remains a continuing need for still further improvement in the materials used to make them, particularly materials that upon curing possess the combined attributes desired to satisfy the increasingly exacting requirements for light management film applications.

BRIEF DESCRIPTION OF THE INVENTION

In one embodiment, a high refractive index monomer comprises compounds according to formula (I)

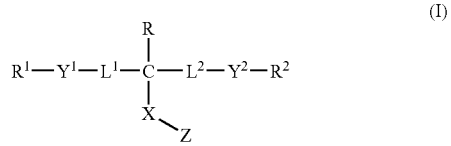

(I)

wherein Z is an ethylenically unsaturated group; X is O, S, or NH; $L^1$ and $L^2$ are each independently $C_1$-$C_3$ alkylene, —($C_1$-$C_3$ alkylene)-S—($C_1$-$C_3$ alkylene)-, or —($C_1$-$C_3$ alkylene)-O—($C_1$-$C_3$ alkylene)-; R is hydrogen or $C_1$-$C_6$ alkyl; $R^1$ and $R^2$ are each independently aryl, including phenyl or naphthyl, aryl($C_1$-$C_6$ alkylene)-, heteroaryl, or heteroaryl ($C_1$-$C_6$ alkylene)-, each of which group is substituted with 0 to 5 substituents independently chosen from halogen, $C_1$-$C_4$alkyl, $C_1$-$C_4$alkoxy, ($C_1$-$C_4$alkyl)S—, $C_1$-$C_4$haloalkyl, and $C_1$-$C_4$haloalkoxy; and $Y^1$ and $Y^2$ are each independently O, S, NH or N, with the proviso that when $Y^1$ and $Y^2$ are both S, i) X is S, ii) at least one of $R^1$ and $R^2$ is heteroaryl or heteroaryl($C_1$-$C_6$ alkylene) substituted as previously described, or iii) one or both of $L^1$ and $L^2$ are—($C_1$-$C_3$ alkylene)-S—($C_1$-$C_3$ alkylene)-, or —($C_1$-$C_3$ alkylene)-O—($C_1$-$C_3$ alkylene)-; and with the proviso that when $Y^1$ or $Y^2$ is N, then each corresponding combination $R^1$—$Y^1$ or $R^1$—$Y^2$ is independently an N-containing heteroaryl excluding carbazole.

In another embodiment, a method of making a high refractive index monomer comprises reacting an aromatic nucleophile $R^1$—$Y^1$H with epichlorohydrin to form a disubstituted 2-propanol according to the formula:

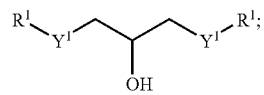

and reacting the disubstituted 2-propanol with an ethylenically unsaturated reactant Z-$X^2$ to form a high refractive index monomer according to the formula:

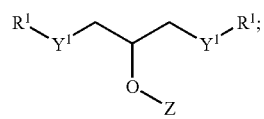

wherein Z is an ethylenically unsaturated group; $X^2$ is a leaving group; each $R^1$ is independently aryl, including phenyl or naphthyl, aryl($C_1$-$C_6$ alkylene)-, heteroaryl, or heteroaryl($C_1$-$C_6$ alkylene)-, each of which group is substituted with 0 to 5 substituents independently chosen from halogen, $C_1$-$C_4$alkyl, $C_1$-$C_4$alkoxy, ($C_1$-$C_4$alkyl)S—, $C_1$-$C_4$haloalkyl, and $C_1$-$C_4$haloalkoxy; each $Y^1$ is independently O, S, NH, or N, with the proviso that when both $Y^1$ groups are S, at least one of the $R^1$ groups is heteroaryl or heteroaryl($C_1$-$C_6$ alkylene) substituted as previously described; or when $Y^1$ is N, then each combination of $R^1$—$Y^1$ is independently a N-containing heteroaryl excluding carbazole.

DETAILED DESCRIPTION

Figure 1:
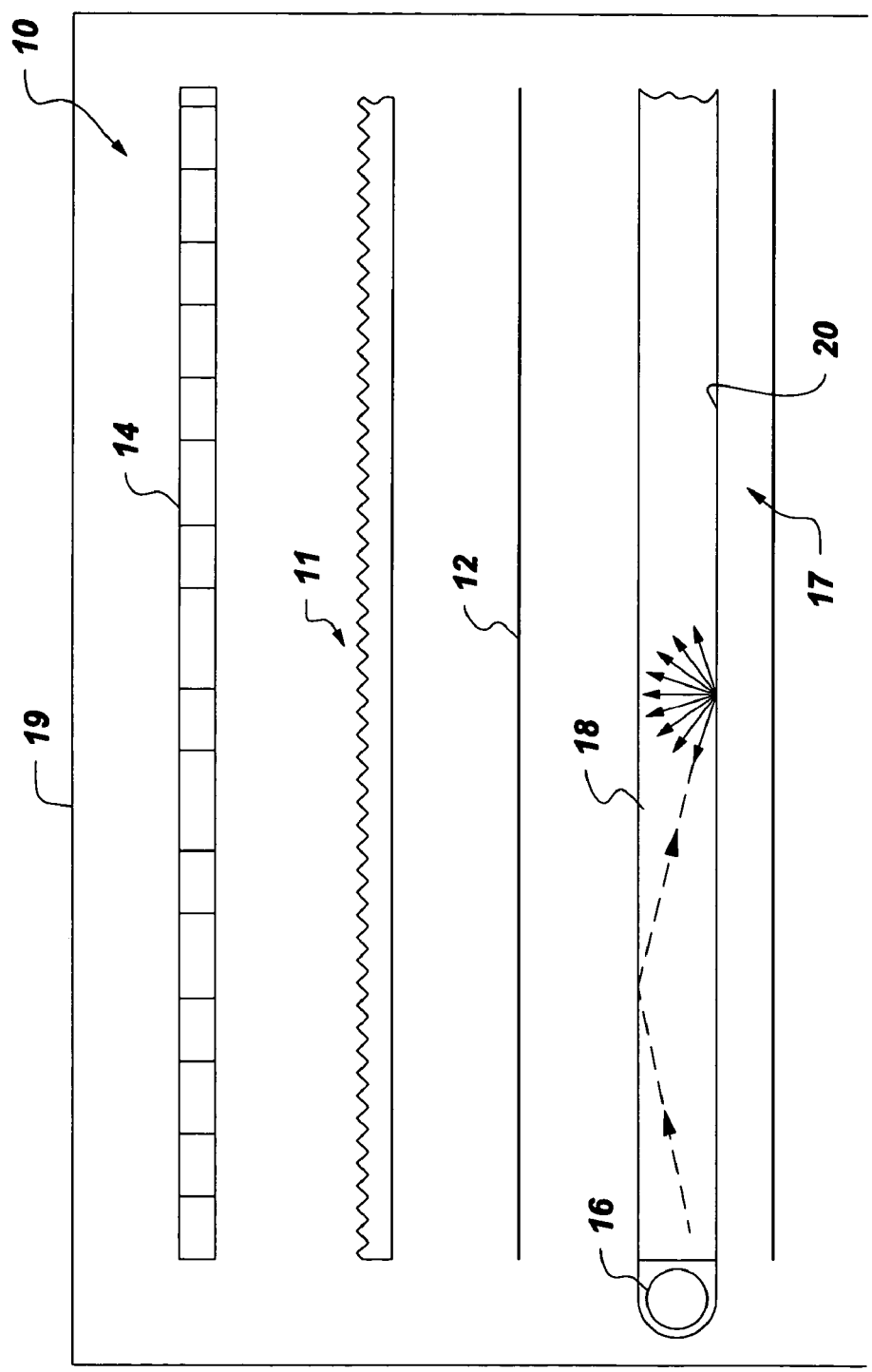
FIG. 1 is a schematic perspective view of a backlit liquid crystal display.

Disclosed herein are high refractive index monomers that, when cured, provide cured materials that also exhibit high refractive indices. The high refractive index monomer may be combined with other monomers, oligomers, and/or polymers to form radiation curable compositions. Also provided herein are low viscosity high refractive index monomers useful in combinations with higher viscosity oligomers and optionally other monomers to provide curable compositions. The curable compositions are ideally suited for the production of optical articles due to their high refractive indices, and ease of processing. Exemplary optical articles include light management films for use in back-light displays;

projection displays; traffic signals; illuminated signs; optical lenses; Fresnel lenses; optical disks; diffuser films; holographic substrates; or as substrates in combination with conventional lenses, prisms or mirrors, and the like.

Also provided herein is a process of preparing high refractive index monomers using epichlorohydrin and aromatic nucleophiles. The method provides a clean and efficient route to a variety of high refractive index monomers exhibiting minimal coloration.

As used herein, "(meth)acrylate" is inclusive of both acrylate and methacrylate functionality.

The terms "a" and "an" herein do not denote a limitation of quantity, but rather denote the presence of at least one of the referenced item. All ranges disclosed herein are inclusive and combinable.

As used herein "high refractive index" means a refractive index of greater than about 1.50.

The high refractive index monomers include those according to formula (I)

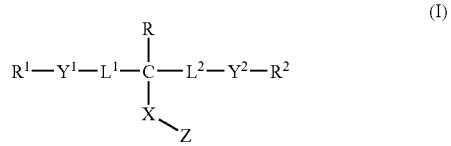

wherein Z is an ethylenically unsaturated group; X is O, S, or NH; $L^1$ and $L^2$ are each independently $C_1$-$C_3$ alkylene, —($C_1$-$C_3$ alkylene)-S—($C_1$-$C_3$ alkylene)-, or —($C_1$-$C_3$ alkylene)-O—($C_1$-$C_3$ alkylene)-; R is hydrogen or $C_1$-$C_6$ alkyl; $R^1$ and $R^2$ are each independently aryl, including phenyl or naphthyl, aryl($C_1$-$C_6$ alkylene)-, heteroaryl, or heteroaryl ($C_1$-$C_6$ alkylene)-, each of which group is substituted with 0 to 5 substituents independently chosen from halogen, $C_1$-$C_4$alkyl, $C_1$-$C_4$alkoxy, ($C_1$-$C_4$alkyl)S—, $C_1$-$C_4$haloalkyl, and $C_1$-$C_4$haloalkoxy; and $Y^1$ and $Y^2$ are each independently O, S, NH, or N, with the proviso that when $Y^1$ or $Y^2$ is N, then each corresponding combination $R^1$—$Y^1$ or $R^1$—$Y^2$ is independently an N-containing heteroaryl. In one embodiment, when $Y^1$ and $Y^2$ are both S, then one of the following occurs: i) X is S, ii) at least one of $R^1$ and $R^2$ is heteroaryl or heteroaryl($C_1$-$C_6$ alkylene) substituted as previously described, or iii) one or both of $L^1$ and $L^2$ are —($C_1$-$C_3$ alkylene)-S—($C_1$-$C_3$ alkylene)-, or —($C_1$-$C_3$ alkylene)-O—($C_1$-$C_3$ alkylene)-. In yet another embodiment, when $Y^1$ or $Y^2$ is N, then each corresponding combination $R^1$—$Y^1$ or $R^1$—$Y^2$ is independently an N-containing heteroaryl excluding carbazole.

Z is an ethylenically unsaturated group, for example, acryloyl, methacryloyl, vinyl, allyl, and the like; more specifically acryloyl and methacryloyl.

The $L^1$ and $L^2$ groups are each independently $C_1$-$C_3$ alkylene, more specifically $C_1$-$C_2$ alkylene, and yet more specifically $C_1$ alkylene. Moreover, the $L^1$ and $L^2$ groups are each independently —($C_1$-$C_3$ alkylene)-S—($C_1$-$C_3$ alkylene)-, or —($C_1$-$C_3$ alkylene)-O—($C_1$-$C_3$ alkylene)-; more specifically, —($C_1$alkylene)-S—($C_2$ alkylene)-, —($C_2$ alkylene)-S—($C_1$alkylene)-, —($C_1$ alkylene)-O—($C_2$ alkylene)-, or —($C_2$ alkylene)-O—($C_1$ alkylene)-; and the like.

The R group can be hydrogen or $C_1$-$C_6$ alkyl, more specifically hydrogen or $C_1$-$C_3$ alkyl, and yet more specifically hydrogen.

The X group can be O, S, or NH; more specifically O or S, and yet more specifically O.

Suitable aryl groups for $R^1$ and $R^1$ include, for example, phenyl and naphthyl groups, each of which group is substituted with 0 to 5 substituents independently chosen from halogen, $C_1$-$C_4$alkyl, $C_1$-$C_4$alkoxy, ($C_1$-$C_4$alkyl)S—, $C_1$-$C_4$haloalkyl, and $C_1$-$C_4$haloalkoxy. Exemplary $R^1$ and $R^2$ groups include phenyl, 3-bromophenyl, 4-bromophenyl, 2,4,6-tribromophenyl, naphthyl, the heteroaryl groups described herein, specifically benzo[d]thiazolyl, benzo[d]oxazolyl, N-phenothiazinyl, and the like.

As used herein, a dash ("—") that is not between two letters or symbols is used to indicate a point of attachment for a substituent. For example, ($C_1$-$C_4$alkyl)S— is attached through the sulfur atom.

As used herein, "alkyl" includes both branched and straight chain saturated aliphatic hydrocarbon groups, having the specified number of carbon atoms. Examples of alkyl include, but are not limited to, methyl, ethyl, n-propyl, isopropyl, n-butyl, 3-methylbutyl, t-butyl, n-pentyl, and sec-pentyl.

As used herein "alkoxy" indicates an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

As used herein "haloalkyl" indicates both branched and straight-chain alkyl groups having the specified number of carbon atoms, substituted with 1 or more halogen atoms, generally up to the maximum allowable number of halogen atoms. Examples of haloalkyl include, but are not limited to, tribromomethyl, dibromomethyl, 2-bromoethyl, and pentabromoethyl.

"Haloalkoxy" indicates a haloalkyl group as defined above attached through an oxygen bridge.

"Halo" or "halogen" as used herein refers to fluoro, chloro, bromo, or iodo.

As used herein, "heteroaryl" indicates a stable aromatic ring which contains from 1 to 3, or preferably from 1 to 2, heteroatoms chosen from N, O, and S, with remaining ring atoms being carbon, or a stable bicyclic or tricyclic system containing at least one 5 to 7 membered aromatic ring which contains from 1 to 3, or preferably from 1 to 2, heteroatoms chosen from N, O, and S, with remaining ring atoms being carbon. When the total number of S and O atoms in the heteroaryl group exceeds 1, these heteroatoms are not adjacent to one another. Examples of heteroaryl groups include, but are not limited to, benzo[d]thiazolyl, benzo[d]oxazolyl, benzofuranyl, benzothiophenyl, benzoxadiazolyl, dihydrobenzodioxynyl, furanyl, imidazolyl, indolyl, isoxazolyl, oxazolyl, N-phenothiazinyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, and triazolyl.

The $Y^1$ and $Y^2$ groups can each independently be O, S, NH, or N, more specifically O or S, and yet more specifically S. In one embodiment, when $Y^1$ and $Y^2$ are both S, X is S. Optionally, when $Y^1$ and $Y^2$ are both S at least one of $R^1$ and $R^2$ is heteroaryl or heteroaryl($C_1$-$C_6$ alkylene) substituted as previously described. Still further, when $Y^1$ and $Y^2$ are both S, one or both of $L^1$ and $L^2$ can be —($C_1$-$C_3$ alkylene)-S—($C_1$-$C_3$ alkylene)-, or —($C_1$-$C_3$ alkylene)-O—($C_1$-$C_3$ alkylene)-.

When $Y^1$ or $Y^2$ is N, then each corresponding combination $R^1$—$Y^1$ or $R^1$—$Y^2$ is independently an N-containing heteroaryl. For the monomers of formula (I) where the combination $R^1$—$Y^1$ or $R^2$—$Y^2$ is an N-containing heteroaryl, the nitrogen of the heteroaryl is covalently bonded to the $L^1$ or $L^2$ group respectively. Suitable N-containing heteroaryls include, for example, N-10H-phenothiazinyl, N-1H-indolyl, benzimidazolyl, imidazolyl, N-9,10-dihydroacridinyl, and the like. In one embodiment when $Y^1$ or $Y^2$ is N, then each corresponding combination $R^1$—$Y^1$ or $R^1$—$Y^2$ excludes carbazole.

Specific examples of high refractive index monomers include 1,3-bis(2-bromophenoxy)propan-2-yl acrylate; 1,3-bis(4-bromophenoxy)propan-2-yl acrylate; 1,3-bis(3-bromophenoxy)propan-2-yl acrylate; 1,3-bis(4-methylphenylthio)-2-propyl acrylate; 1,3-bis(phenoxy)propan-2-yl acrylate; 1,3-bis(2-mercaptobenzothiazoyl)-2-propyl acrylate or 1,3-bis(benzo[d]thiazol-2-ylthio)propan-2-yl acrylate; 1,3-bis(2,4,6-tribromophenoxy)-2-propyl acrylate; 1,3-bis(phenylthio)propan-2-yl acrylate; 1,3-bis(4-bromophenylthio)propan-2-yl acrylate; 1,3-bis(3-bromophenylthio)propan-2-yl acrylate; 1,3-bis(2,4,6-tribromophenylthio)propan-2-yl acrylate; 1,3-di(10H-phenothiazin-10-yl)propan-2-yl acrylate; 1,3-bis(2-(phenylthio)ethylthio)propan-2-yl acrylate; 1-phenoxy-3-(phenylthio)propan-2-yl acrylate; 1-(4-chlorophenoxy)-3-(phenylthio)propan-2-yl acrylate; 1-(4-bromophenoxy)-3-(4-bromophenylthio)propan-2-yl acrylate; 1-(2,4,6-tribromophenoxy)-3-(2,4,6-tribromophenylthio)propan-2-yl acrylate; or 1-(2,4-dibromophenoxy)-3-(2,4-dibromophenylthio)propan-2-yl acrylate.

The high refractive index monomers exhibit a range of viscosities depending upon the substitution. Those monomers having a range of viscosity from about 1 centaPoise (cP) to about 1000 cP are suitable as monomer diluents due to their low viscosity. Such monomers may be used in curable compositions containing higher viscosity oligomeric materials to provide curable compositions having a desired viscosity for ease of processing. The high refractive index monomers useful as diluents exhibit a viscosity of about 1 centaPoise (cP) to about 1000 cP, more specifically about 5 cP to about 700 cP, and yet more specifically about 10 cP to about 400 cP measured using a Brookfield LVDV-II Cone/Plate Viscometer at 25° C.

The high refractive index monomers generally exhibit a refractive index of greater than or equal to about 1.50, more specifically greater than or equal to about 1.55, and yet more specifically greater than or equal to about 1.60.

The high refractive index monomers may be prepared by a number of methods including a nucleophilic substitution reaction between an aromatic nucleophile and a compound having the desired carbon scaffold

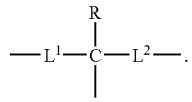

Usually the reaction is performed in the presence of a base to result in a disubstituted alcohol, thiol, or primary amine according to the formula (II):

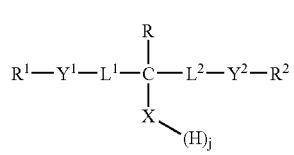

(II)

wherein j is 1 when X is NH, S or O and 2 when X is N. The resulting disubstituted alcohol, thiol, or primary amine may then be functionalized with an ethylenically unsaturated group, such as acryloyl, to result in a high refractive index monomer. An exemplary reaction includes the reaction of 1,3-dibromopropan-2-ol with phenylthiol in the presence of a base to form 1,3-bis(phenylthio)propan-2-ol. The intermediate, 1,3-bis(phenylthio)propan-2-ol, may then be reacted with acryloyl chloride to result in a high refractive index monomer 1,3-bis(phenylthio)propan-2-yl acrylate.

A more efficient and clean process to prepare the high refractive index monomer is the reaction of epichlorohydrin and aromatic nucleophiles. To prepare symmetric monomers, an aromatic nucleophile is first reacted with epichlorohydrin in about a two to one molar ratio of nucleophile to epichlorohydrin in the presence of a stoichometric amount of base relative to the aromatic nucleophile. The reaction product substantially includes a symmetrically disubstituted 2-propanol as described in Scheme I:

Scheme I

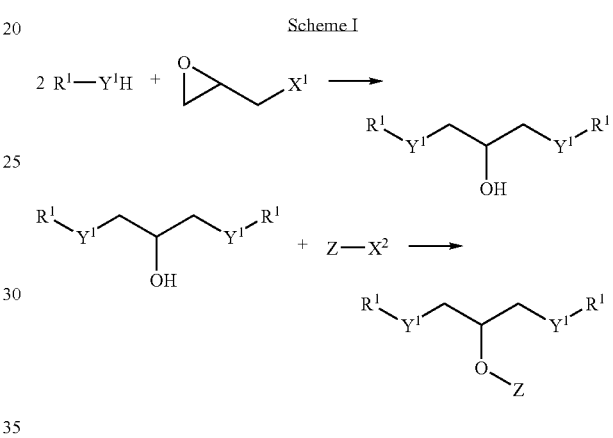

In a second step, the symmetrically disubstituted 2-propanol is reacted with an ethylenically unsaturated reactant $Z$-$X^2$ to provide a symmetrical high refractive index monomer. In Scheme I, $Y^1$, $R^1$, and Z are as defined previously; $X^1$ is a halogen, and $X^2$ is a leaving group such as a halogen.

A method to prepare asymmetric high refractive index monomers is described in Scheme II:

Scheme II

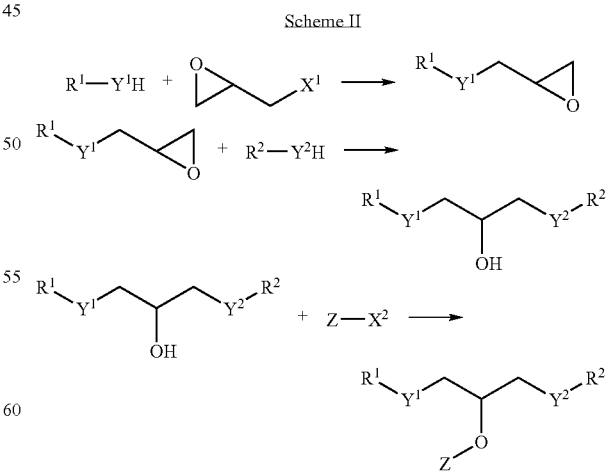

In a first step, an aromatic nucleophile, $R^1$—$Y^1$H, is first reacted with epichlorohydrin using an excess of epichlorohydrin to form a 2-substituted oxirane. Again the reaction is performed in the presence of a stoichometric amount of base relative to the nucleophile. The 2-substituted oxirane is isolated prior to the reaction with a second aromatic nucleophile, $R^2$—$Y^2H$, to form an asymmetrically disubstituted 2-propanol. The asymmetrically disubstituted 2-propanol is further reacted with an ethylenically unsaturated reactant Z-$X^2$ to provide the monomer product. The groups $Y^1$, $Y^2$, $R^1$, $R^2$, Z, $X^1$ and $X^2$ are as defined previously.

In another embodiment, rather than a two-step process to form the disubstitued 2-propanol, a combination of nucleophiles $R^1$—$Y^1H$ and $R^2$—$Y^2H$ are allowed to react with epichlorohydrin to form a mixture of disubstituted 2-propanol products. The mixture contains a combination of reaction products including both asymmetric and symmetric disubstituted 2-propanol:

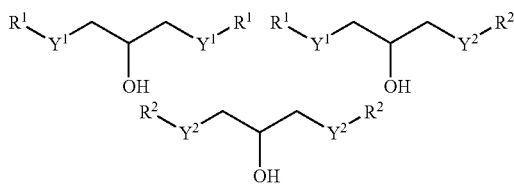

The mixture of disubstituted 2-propanol products is then further reacted with an ethylenically unsaturated reactant Z-$X^2$ to provide a mixture of monomer products.

Typically in the reaction to prepare the high refractive index monomers, the product contains impurities resulting in a colored, and sometimes a highly colored, product. It has been found that the process preparing the monomer via the epichlorohydrin route combined with a purification step using nonpolar solvents results in a convenient route to clean, low color monomer. The removal of color from the prepared high refractive index monomer may be effected by the addition of a nonpolar solvent, such as hexanes, petroleum ether, and the like, that results in the precipitation of color forming side products. The low color product can be obtained by removing the precipitated color bodies by filtration or decanting the dissolved crude acrylate. To further reduce the color, the filtrate can be passed over a solid adsorbent such as silica or alumina, which further reduces the color.

Low color of the curable coating compositions is desired as absorption of visible light leads to a reduction in brightness of light management films prepared from such compositions. By using low color monomers in the curable coating compositions, it is possible to prepare low color cured materials, thereby resulting in good brightness in light management films.

In one aspect, one or more high refractive index monomers may be combined with curable oligomers, and/or additional monomers to form a radiation curable composition. Such compositions are solventless and when cured provides a material having an excellent balance of properties. The curable compositions are ideally suited for the preparation of optical articles including light management film applications.

The curable compositions may comprise a multifunctional (meth)acrylate, i.e., a molecule containing at least two (meth)acrylate functional groups. In a preferred embodiment, the multifunctional (meth)acrylate is represented by the formula (III)

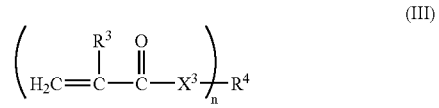

wherein $R^3$ is hydrogen or methyl; $X^3$ is O or S; $R^4$ is substituted or unsubstituted $C_1$-$C_{300}$ alkyl, aryl, alkaryl, arylalkyl, or heteroaryl; and n is 2, 3, or 4. The substitution on $R^4$ includes, but is not limited to, halo, $C_1$-$C_6$ alkyl, $C_1$-$C_3$ haloalkyl, $C_1$-$C_4$ haloalkoxy, ($C_1$-$C_4$alkyl)S—, hydroxy, $C_1$-$C_6$ ketone, $C_1$-$C_6$ ester, N,N—($C_1$-$C_3$) alkyl substituted amide, or a combination thereof. Preferred $R^4$ groups include such groups as alkylene and hydroxy alkylene disubstituted bisphenol-A or bisphenol-F ethers, especially the brominated forms of bisphenol-A and -F. Suitable $R^4$ groups include those according to the formula (IV)

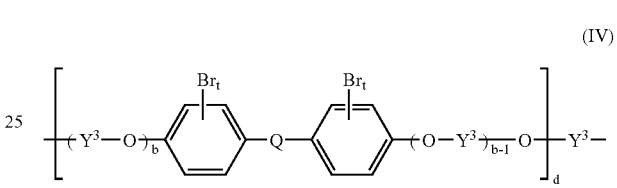

wherein Q is —C(CH$_3$)$_2$—, —CH$_2$—, —C(O)—, —S(O)—, —S—, —O—, or —S(O)$_2$—; $Y^3$ is $C_1$-$C_6$ branched or straight chain alkylene, hydroxy substituted $C_1$-$C_6$ alkylene; b is independently at each occurrence 1 to 10; t is independently at each occurrence 0, 1, 2, 3, or 4; and d is about 1 to about 3.

The multifunctional (meth)acrylates may include compounds produced by the reaction of (meth)acrylic acid or hydroxy substituted (meth)acrylate with a di-epoxide, such as bisphenol-A diglycidyl ether; bisphenol-F diglycidyl ether; tetrabromo bisphenol-A diglycidyl ether; tetrabromo bisphenol-F diglycidyl ether; 1,3-bis-{4-[1-methyl-1-(4-oxiranylmethoxy-phenyl)-ethyl]-phenoxy}-propan-2-ol; 1,3-bis-{2,6-dibromo-4-[1-(3,5-dibromo-4-oxiranylmethoxy-phenyl)-1-methyl-ethyl]-phenoxy }-propan-2-ol; 1-(3-(2-(4-((oxiran-2-yl)methoxy)phenyl)propan-2-yl)phenoxy)-3-(4-(2-(4-((oxiran-2-yl)methoxy)phenyl)propan-2-yl)phenoxy) propan-2-ol; and the like; and a combination thereof. Examples of such compounds include acrylic acid 3-(4-{1-[4-(3-acryloyloxy-2-hydroxy-propoxy)-3,5,-dibromo-phenyl]-1-methyl-ethyl}-2,6-dibromo-phenoxy)-2-hydroxy-propyl ester; acrylic acid 3-[4-(1-{4-[3-(4-{1-[4-(3-acryloyloxy-2-hydroxy-propoxy)-3,5-dibromo-phenyl]-1-methyl-ethyl}-2,6-dibromo-phenoxy)-2-hydroxy-propoxy]-3,5-dibromo-phenyl}-1-methyl-ethyl)-2,6-dibromo-phenoxy]-2-hydroxy-propyl ester; and the like, and a combination thereof.

Other exemplary multifunctional (meth)acrylates include 2,2-bis(4-(2-(meth)acryloxyethoxy)phenyl)propane; 2,2-bis((4-(meth)acryloxy)phenyl)propane; 2,2-bis(4-(meth)acryloyloxydiethoxyphenyl)propane; 2,2-bis(4-(meth)acryloyloxytriethoxyphenyl)propane; 2,2-bis(4-(meth)acryloyloxytetraethoxyphenyl)propane; 2,2-bis(4-(meth)acryloyloxypentaethoxyphenyl)propane; 2,2-bis(4-(meth)acryloyloxyethoxy-3,5-dibromophenyl)propane; 2,2-bis(4-(meth)acryloyloxydiethoxy-3,5-dibromophenyl)propane; bis(4-(meth)acryloyloxypentaethoxy-3,5-dibromophenyl) propane; bis(4-(meth)acryloyloxyphenyl)methane; bis(4-

(meth)acryloyloxyethoxyphenyl)methane; bis(4-(meth)acryloyloxydiethoxyphenyl)methane; bis(4-(meth)acryloyloxytriethoxyphenyl)methane; bis(4-(meth)acryloyloxytetraethoxyphenyl)methane; bis(4-(meth)acryloyloxypentaethoxyphenyl)methane; bis(4-(meth)acryloyloxydiethoxyphenyl)sulfone; bis(4-(meth)acryloyloxypentaethoxyphenyl)sulfone; bis(4-(meth)acryloyloxydiethoxyphenyl)sulfide; bis(4-(meth)acryloyloxypentaethoxyphenyl)sulfide; bis(4-(meth)acryloyloxydiethoxy-3,5-dimethylphenyl)sulfide; bis(4-(meth)acryloyloxypentaethoxy-3,5-dimethylphenyl)sulfide; and the like.

A suitable multifunctional (meth)acrylate based on the reaction product of tetrabrominated bisphenol-A di-epoxide and acrylic acid is RDX 51027 available from UCB Chemicals. Other commercially available multifunctional (meth)acrylates include EB600, EB3600, EB3605, EB3700, EB3701, EB3702, EB3703, and EB3720, all available from UCB Chemicals, or CN104 and CN120 available from Sartomer.

In one embodiment the multifunctional (meth)acrylate comprises a urethane (meth)acrylate. Such materials can be prepared, for example, by the reaction of 2 molar equivalence of an alkylene diisocyanate of the formula OCN—$R^5$—NCO with 1 molar equivalence of a diol of the formula HO—$R^6$—OH, wherein each of $R^5$ and $R^6$ is independently a $C_{2-100}$ alkylene group, to form a urethane diol diisocyanate, followed by reaction with a hydroxyalkyl (meth)acrylate. For example, a preferred compound is a the product of reaction of an aromatic diisocyanate (e.g. TDI) with a polyester diol followed by reaction with hydroxyalkyl acrylate. Also contemplated are the thiol versions of the above urethane (meth)acrylate prepared from dithiols of the formula HS—$R^6$—SH. Such materials containing sulfur atoms provide an increase in refractive index of the multifunctional (meth)acrylate, and, in turn, increases the refractive index of the resulting curable compositions.

Other multifunctional (meth)acrylates include, for example, polyol poly(meth)acrylates, which are typically prepared from aliphatic diols, triols and/or tetraols containing 2-100 carbon atoms. Examples of suitable poly(meth)acrylates are ethylene glycol diacrylate, 1,6-hexanediol diacrylate, neopentylglycol di(meth)acrylate, ethyleneglycol di(meth)acrylate, polyethyleneglycol (n=2-15) di(meth)acrylate, polypropyleneglycol (n=2-15) di(meth)acrylate, polybutyleneglycol (n=2-15) di(meth)acrylate, 2,2-bis(4-(meth)acryloxyethoxyphenyl) propane, 2,2-bis(4-(meth)acryloxydiethoxyphenyl) propane, 2,2-bis(4-(meth)acryloxyethoxy-3,5-dibromophenyl) propane, pentaerythritol tri(meth)acrylate, pentaerythritol tetra(meth)acrylate, dipentaerythritol penta(meth)acrylate, dipentaerythritol hexa(meth)acrylate, 2-ethyl-2-hydroxymethyl-1,3-propanediol tri(meth)acrylate (trimethylolpropane tri(meth)acrylate), di(trimethylolpropane) tetra(meth)acrylate, and the (meth)acrylates of alkoxylated (usually ethoxylated) derivatives of said polyols. Also included are N,N'-alkylenebisacrylamides, specifically those containing a $C_{1-4}$ alkylene group.

One or more multifunctional (meth)acrylates may be used to prepare the curable composition. The multifunctional (meth)acrylate may be present in the curable composition in an amount of about 25 to about 75 weight percent based on the total composition, specifically about 35 to about 70, more specifically about 45 to about 65, and yet more specifically about 50 to about 60 weight percent based on the total composition.

The curable composition may further comprise an additional substituted or unsubstituted (meth)acrylate monomer (hereinafter "additional (meth)acrylate monomer"). The additional (meth)acrylate monomers include alkyl, cycloalkyl, aryl, and heteroaryl mono-substituted (meth)acrylate compounds.

An exemplary additional (meth)acrylate monomer is represented by the formula (V)

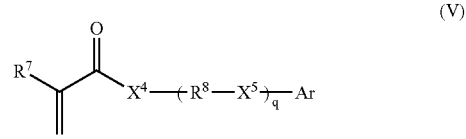

wherein $R^7$ is hydrogen or methyl; $X^4$ is O, S or NH; each occurrence of $X^5$ is O, S, NH, or a chemical bond linking adjacent groups; wherein each occurrence of $R^8$ is substituted or unsubstituted $C_1$-$C_6$ alkyl or alkenyl; q is 0, 1, 2, or 3; Ar is substituted or unsubstituted $C_6$-$C_{12}$ aryl including phenyl, or $C_6$-$C_{12}$ heteroaryl; wherein the substitution on the $R^8$ and Ar independently include aryl, halo, $C_1$-$C_6$ alkyl, $C_1$-$C_4$ haloalkyl, $C_1$-$C_4$ haloalkoxy, ($C_1$-$C_4$alkyl)S—, hydroxy, $C_1$-$C_6$ ketone, $C_1$-$C_6$ ester, N,N—($C_1$-$C_3$) alkyl substituted amide, or a combination thereof. The Ar group, when substituted, may be mono-, di-, tri-, tetra- or penta-substituted.

Exemplary additional (meth)acrylate monomers include 2-phenoxyethyl (meth)acrylate; 2-phenylthioethyl (meth)acrylate; phenyl (meth)acrylate; 2-, 3,-, and 4-bromophenyl (meth)acrylate; 2,4,6-tribromophenyl (meth)acrylate; tetrabromophenyl (meth)acrylate; pentabromophenyl (meth)acrylate; benzyl (meth)acrylate; 2-, 3,-, and 4-bromobenzyl (meth)acrylate; 2,4,6-tribromobenzyl (meth)acrylate; tetrabromobenzyl (meth)acrylate; pentabromobenzyl (meth)acrylate; methyl (meth)acrylate; butyl (meth)acrylate; 2-hydroxyethyl (meth)acrylate; cyclohexyl (meth)acrylate; tetrahydrofurfuryl (meth)acrylate; dicyclopentanyl (meth)acrylate; dicyclopentenyl (meth)acrylate; 3-phenyl-2-hydroxypropyl (meth)acrylate; ortho-biphenyl (meth)acrylate; 3-(2,4-dibromophenyl)-2-hydroxypropyl (meth)acrylate; and the like.

In one aspect, the curable composition may comprise two or more additional (meth)acrylate monomers. The additional (meth)acrylate monomer may be present in the curable composition in an amount of 0 to about 30, specifically about 1 to about 20 and more specifically about 3 to about 15 weight percent based on the total weight of the composition.

The curable composition may further comprise a polymerization initiator to promote polymerization of the ethylenically unsaturated components. Suitable polymerization initiators include photoinitiators that promote polymerization of the components upon exposure to ultraviolet radiation. Particularly suitable photoinitiators include phosphine oxide photoinitiators. Examples of such photoinitiators include the IRGACURE® and DAROCUR™ series of phosphine oxide photoinitiators available from Ciba Specialty Chemicals; the LUCIRIN® series from BASF Corp.; and the ESACURE® series of photoinitiators. Other useful photoinitiators include ketone-based photoinitiators, such as hydroxy- and alkoxyalkyl phenyl ketones, and thioalkylphenyl morpholinoalkyl ketones. Also suitable are benzoin ether photoinitiators.

The polymerization initiator may include peroxy-based initiators that may promote polymerization under thermal activation. Examples of useful peroxy initiators include, for example, benzoyl peroxide, dicumyl peroxide, methyl ethyl ketone peroxide, lauryl peroxide, cyclohexanone peroxide, t-butyl hydroperoxide, t-butyl benzene hydroperoxide, t-butyl peroctoate, 2,5-dimethylhexane-2,5-dihydroperoxide, 2,5-dimethyl-2,5-di(t-butylperoxy)-hex-3-yne, di-t-butylperoxide, t-butylcumyl peroxide, alpha,alpha'-bis(t-butylperoxy-m-isopropyl)benzene, 2,5-dimethyl-2,5-di(t-butylperoxy)hexane, dicumylperoxide, di(t-butylperoxy isophthalate, t-butylperoxybenzoate, 2,2-bis(t-butylperoxy) butane, 2,2-bis(t-butylperoxy)octane, 2,5-dimethyl-2,5-di (benzoylperoxy)hexane, di(trimethylsilyl)peroxide, trimethylsilylphenyltriphenylsilyl peroxide, and the like, and a combination thereof.

The polymerization initiator may be used in an amount of about 0.01 to about 10 weight percent based on the total weight of the composition, specifically about 0.1 weight percent to about 5 weight percent, more specifically about 0.5 weight percent to about 3 weight percent.

The composition may, optionally, further comprise an additive selected from flame retardants, antioxidants, thermal stabilizers, ultraviolet stabilizers, dyes, colorants, antistatic agents, surfactant, and the like, and a thereof, so long as they do not deleteriously affect the polymerization of the composition.

In one embodiment, a curable coating composition comprises (a) a high refractive index monomer according to formula (I)

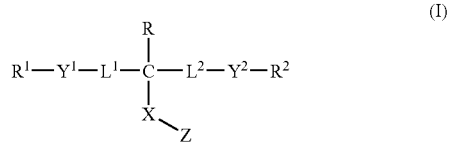

wherein Z is an acryloyl or methacryloyl group; X is O or S; $L^1$ and $L^2$ are each independently $C_1$-$C_3$ alkylene, —($C_1$-$C_3$ alkylene)-S—($C_1$-$C_3$ alkylene)-, or —($C_1$-$C_3$ alkylene)-O—($C_1$-$C_3$ alkylene)-; R is hydrogen; $R^1$ and $R^2$ are each independently phenyl, phenyl($C_1$-$C_6$ alkylene)-, or naphthyl, each of which is substituted with 0 to 5 bromo substituents; heteroaryl or heteroaryl($C_1$-$C_6$ alkylene)-, wherein the heteroaryl is benzo[d]thiazolyl, benzo[d]oxazolyl, benzofuranyl, benzothiophenyl, benzoxadiazolyl, dihydrobenzodioxynyl, furanyl, imidazolyl, indolyl, isoxazolyl, oxazolyl, N-phenothiazinyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, or triazolyl; and $Y^1$ and $Y^2$ are each independently O, S, or N, with the proviso that when $Y^1$ and $Y^2$ are both S, i) X is S, ii) at least one of $R^1$ and $R^2$ is heteroaryl or heteroaryl($C_1$-$C_6$ alkylene), or iii) one or both of $L^1$ and $L^2$ are —($C_1$-$C_3$ alkylene)-S—($C_1$-$C_3$ alkylene)-, or —($C_1$-$C_3$ alkylene)-O— ($C_1$-$C_3$ alkylene)-; and with the proviso that when $Y^1$ or $Y^2$ is N, then each corresponding combination $R^1$—$Y^1$ or $R^1$—$Y^2$ is independently an N-containing heteroaryl excluding carbazole wherein the N-containing heteroaryl is N-10H-phenothiazinyl, N-1H-indolyl, benzimidazolyl, imidazolyl, or N-9,10-dihydroacridinyl; (b) a multifunctional (meth)acrylate; (c) an optional additional (meth)acrylate; and (d) a polymerization initiator.

When the high refractive index monomers are used in curable compositions, the refractive index of the cured composition may be greater than or equal to about 1.50, more specifically greater than or equal to about 1.53, and yet more specifically greater than or equal to about 1.55.

The curable composition may be prepared by simply blending the components thereof, with efficient mixing to produce a homogeneous mixture. When forming articles from the curable composition, it is often preferred to remove air bubbles by application of vacuum or the like, with gentle heating if the mixture is viscous. The composition can then be charged to a mold that may bear a microstructure to be replicated and polymerized by exposure to ultraviolet radiation or heat to produce a cured article.

An alternative method includes applying the radiation curable, uncured, composition to a surface of a base film substrate, passing the base film substrate having the uncured composition coating through a compression nip defined by a nip roll and a casting drum having a negative pattern master of the microstructures. The compression nip applies a sufficient pressure to the uncured composition and the base film substrate to control the thickness of the composition coating and to press the composition into full dual contact with both the base film substrate and the casting drum to exclude any air between the composition and the drum. The radiation curable composition is cured by directing radiation energy through the base film substrate from the surface opposite the surface having the composition coating while the composition is in full contact with the drum to cause the microstructured pattern to be replicated in the cured composition layer. This process is particularly suited for continuous preparation of a cured composition in combination with a substrate.

The curable compositions can be cured by UV radiation. The wavelength of the UV radiation may be from about 1800 angstroms to about 4000 angstroms. Suitable wavelengths of UV radiation include, for example, UVA, UVB, UVC, UVV, and the like; the wavelengths of the foregoing are well known in the art. The lamp systems used to generate such radiation include ultraviolet lamps and discharge lamps, as for example, xenon, metallic halide, metallic arc, low or high pressure mercury vapor discharge lamp, etc. Curing is meant both polymerization and cross-linking to form a non-tacky material.

When heat curing is used, the temperature selected may be about 80° to about 130° C. Within this range, a temperature of greater than or equal to about 90° C. may be preferred. Also within this range, a temperature of greater than or equal to about 100° C. may be preferred. The heating period may be of about 30 seconds to about 24 hours. Within this range, it may be preferred to use a heating time of greater than or equal to about 1 minute, more preferably greater than or equal to about 2 minutes. Also within this range, it may be preferred to use a heating time of less than or equal to about 10 hours, more preferably less than or equal to about 5 hours, yet more preferably less than or equal to about 3 hours. Such curing may be staged to produce a partially cured and often tack-free composition, which then is fully cured by heating for longer periods or temperatures within the aforementioned ranges.

In one embodiment, the composition may be both heat cured and UV cured.

In another embodiment, the composition is subjected to a continuous process to prepare a cured film material in combination with a substrate.

Other embodiments include the reaction product obtained by curing any of the above curable compositions.

Still other embodiments include articles made from any of the cured compositions. Articles that may be fabricated from the compositions include, for example, optical articles, such as light management films (LMF) for use in back-light displays; projection displays; traffic signals; illuminated signs; optical lenses; Fresnel lenses; optical disks; diffuser films; holographic substrates; or as substrates in combination with conventional lenses, prisms or mirrors.

Referring to FIG. 1, a backlit liquid crystal display generally indicated at 10 includes an optical management article 11. The optical management article 11 is shown positioned between a diffuser 12 and a liquid crystal display panel 14. The backlit liquid crystal display also includes a light source 16 such as a fluorescent lamp, a light guide 18 for transporting light for reflection toward the liquid crystal display panel 14, and a white reflector 17 for reflecting light also toward the liquid crystal display panel 14. The optical management article 11 collimates light emitted from the light guide 18 thereby increasing the brightness of the liquid crystal display panel 14, enabling a sharper image to be produced by the liquid crystal display panel and allowing the power of the light source 16 to be reduced to produce a selected brightness. The optical management article 11 in the backlit liquid crystal display is useful in equipment such as computers, personal televisions, video recorders, mobile communication devices, and automobile and avionic instrument displays.

Figure 2:
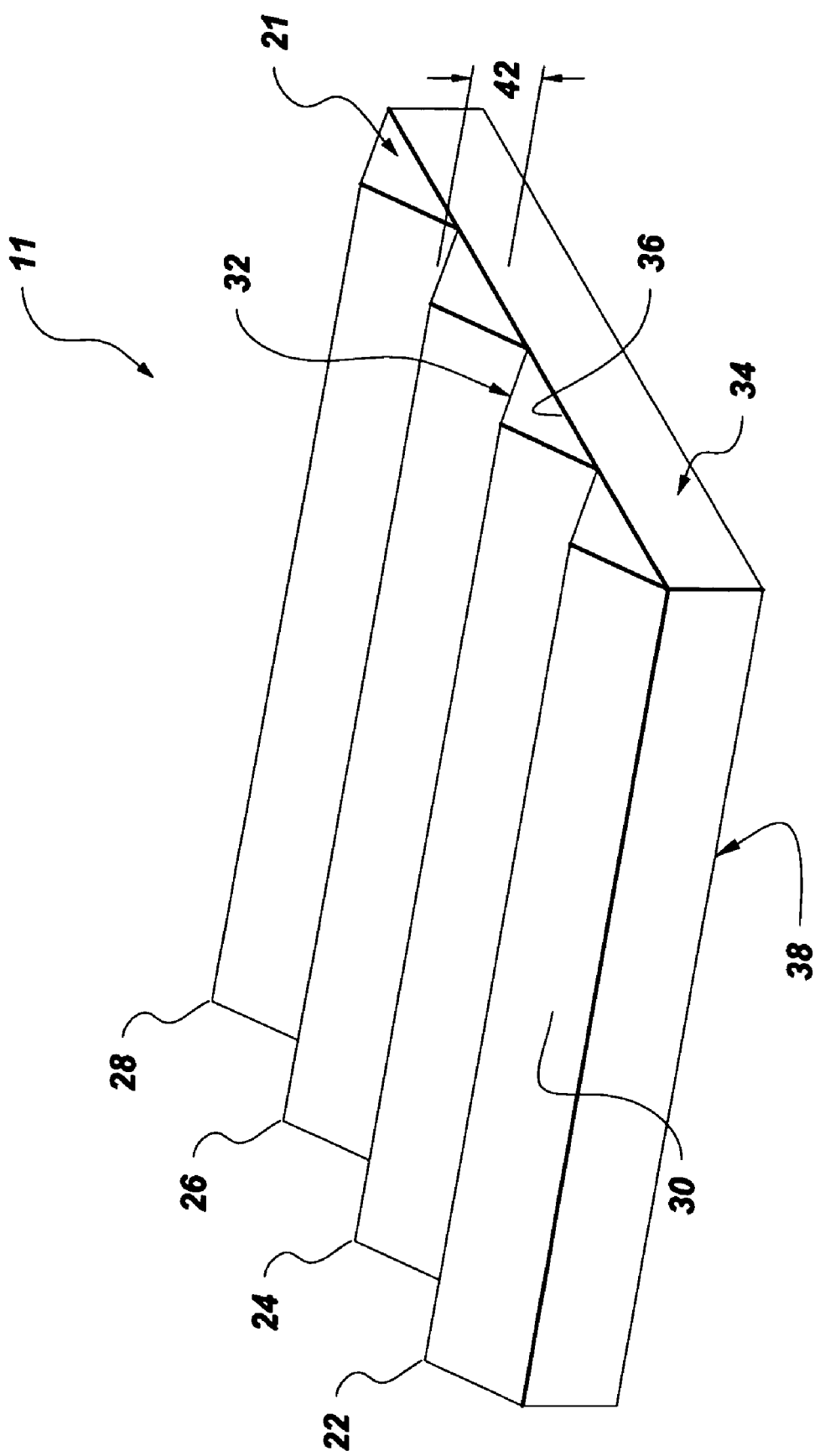
FIG. 2 is a schematic perspective view of a light management film displaying the microstructure and supporting polymeric substrate.

The optical management article 11 includes LMF 21 comprising an array of prisms typified by prisms 22, 24, 26, and 28, as illustrated in FIG. 2. Each prism, for example, has a first facet 30 and a second facet 32. The prisms 22, 24, 26, and 28 are formed on a substrate 34 that has a first surface 36 on which the prisms are formed and a second surface 38 that is substantially flat or planar and opposite the first surface.

The invention is further illustrated by the following non-limiting examples.

EXAMPLES

For Examples 1-5, all reagents were purchased from Aldrich and used without further purification. The reactions were followed and all products identified by $^1$H-NMR spectroscopy using a Bruker Avance 400 MHz NMR.

Example 1

Synthesis of 1,3-bis(phenoxy)propan-2-yl acrylate (BisPEA)

To a 1000 ml flask equipped with a mechanical stirrer, water bath, an addition funnel, a water-jacketed condenser and nitrogen sparge was added 50 grams (g.) of phenol and a solution of 29.68 g. of potassium hydroxide dissolved in about 600 ml of isopropanol. 24.6 g. of epichlorohydrin was added dropwise to the rapidly stirring solution. After the addition, the reaction mixture was heated to 65° C. and the reaction progress monitored periodically by $^1$H-NMR. Upon completion of the reaction, the solution was allowed to cool to room temperature. The contents of the flask was poured into a separatory funnel together with distilled water and ethyl ether in volumes that produced similar volume between the organic layer and the aqueous layer. The aqueous layer was drawn off and the organic layer was washed sequentially with water, dilute sodium hydroxide, dilute HCl, and again with water. The organic layer was dried over MgSO$_4$ and the solvents were removed by rotary evaporation to provide a white crystalline solid. The composition of the isolated product, 1,3-bis(phenoxy)-2-propanol, was confirmed by $^1$H-NMR spectroscopy.

To a 500 ml flask equipped with a mechanical stirrer, oil bath, an addition funnel, a water-jacketed condenser and nitrogen sparge was added 40.10 g. of 1,3-bis(phenoxy)-2-propanol and about 200 ml of toluene. Upon dissolution, about 50 g of toluene was distilled from the solution using a dean stark trap to dry the solution. The solution was allowed to cool, then, 18.20 g. of triethylamine and 0.50 g. of dimethylaminopryridine were added to the mixture. An ice bath was placed on the reaction mixture, then, 16.32 g. of acryloyl chloride was added to the solution dropwise. The mixture was allowed to stir for approximately 48 hours at room temperature and completion of the reaction was confirmed by $^1$H-NMR spectroscopy. The contents of the flask was poured into a separatory funnel together with distilled water and ethyl ether in volumes that produced similar volume between the organic layer and the aqueous layer. The aqueous layer was drawn off and the organic layer was washed several times with water, dilute sodium hydroxide, and dilute HCl until the both the organic layer and the aqueous layer were relatively clear. The organic layer was dried over MgSO$_4$ and the solvents were removed by rotary evaporation to provide a transparent liquid. The composition of the isolated product, 1,3-bis(phenoxy)propan-2-yl acrylate, was confirmed by $^1$H-NMR spectroscopy.

Example 2

Synthesis of 1,3-bis(2-mercaptobenzothiazoyl)propan-2-yl acrylate (BisBTZA)

To a 1000 ml flask equipped with a mechanical stirrer, water bath, an addition funnel, a water-jacketed condenser and nitrogen sparge was added 40 g. of 2-mercaptobenzothiazole and about 500 ml of tetrahydrofuran. Upon dissolution, 1.09 g. of boron trifluoride:etherate was added. Next, 22.1 g. of epichlorohydrin was added dropwise to prevent the solution temperature from exceeding 60° C. A solution containing 40 g. of 2-mercaptobenzothiazole dissolved in 107 g. of tetrahydrofuran was added to the mixture and the solution heated to 50° C. A solution of 25 g. of triethylamine and 25 g. tetrahydrofuran was then added dropwise. Since no exotherm or precipitate was observed upon the addition of the triethylamine, 13.38 g. of potassium hydroxide dissolved in tetrahydrofuran was added dropwise which resulted in an exotherm and the formation of a precipitate. The reaction mixture was stirred at 50° C. and monitored by $^1$H-NMR. Upon completion of the reaction, the solution was allowed to cool to room temperature. The contents of the flask was poured into a separatory funnel together with distilled water and ethyl ether in volumes that produced similar volume between the organic layer and the aqueous layer. The aqueous layer was drawn off and the organic layer was washed several times with water, dilute sodium hydroxide, and dilute HCl until the both the organic layer and the aqueous layer were relatively clear. The organic layer was dried over MgSO$_4$ and the solvents removed by rotary evaporation to provide a viscous liquid. The composition of the isolated product, 1,3-bis(2-mercaptobenzothiazoyl)-2-propanol, was confirmed by $^1$H-NMR spectroscopy. The refractive index was measured with an Abbe refractometer and determined to be 1.6552.

The 1,3-bis(2-mercaptobenzothiazoyl)-2-propanol was reacted with acryloyl chloride in the presence of triethylamine and dimethylaminopryridine according to the procedure in Example 1, but the addition of the acryloyl chloride was performed at room temperature. The composition of the isolated product, 1,3-bis(2-mercaptobenzothiazoyl)propan-2-yl acrylate, was confirmed by $^1$H-NMR spectroscopy.

Example 3

Synthesis of
1,3-bis(2,4,6-tribromophenoxy)propan-2-yl acrylate
(BisTBrPEA)

The intermediate 1,3-bis(2,4,6-tribromophenoxy)-2-propanol was prepared according to the procedure provided in Example 1 using 2,4,6-tribromophenol in place of phenol.

To a 300 ml flask equipped with a mechanical stirrer, oil bath, an addition funnel, a water-jacketed condenser and nitrogen sparge was added 10.26 g. of 1,3-bis(2,4,6-tribromophenoxy)-2-propanol and about 150 g. of tetrahydrofuran. Upon dissolution, the solution was turbid and contained very small amount of insoluble material. As a result, the solution was filtered to remove the precipitate and clarify the solution. Next, 1.46 g. of triethylamine and 0.14 g of dimethylaminopryridine was added to the mixture. Then, 1.31 g. of acryloyl chloride was quickly added to the rapidly stirring solution. The mixture was heated to 50° C. and reaction progress monitored by $^1$H-NMR spectroscopy. After a few hours of monitoring, the reaction progress appeared to have stopped. As a result, another 1.46 g. of triethylamine was charged to the reaction mixture immediately followed by a 1.31 g. charge of acryloyl chloride and the reaction allowed to stir at 50° C. for an additional 14 hours. After this time, it was determined that the reaction had progressed was but was not complete. Thus, another 1.46 g. of triethylamine was charged to the reaction mixture immediately followed by a 1.31 g. charge of acryloyl chloride and the reaction allowed to stir at 50° C. for about an additional 24 hours. After this period, the reaction was complete. The contents of the flask was poured into a separatory funnel together with distilled water and ethyl ether in volumes that produced similar volume between the organic layer and the aqueous layer. The aqueous layer was drawn off and the organic layer was washed several times with water, dilute sodium hydroxide, and dilute HCl until the both the organic layer and the aqueous layer were relatively clear. The organic layer was dried over MgSO$_4$ and the solvents were removed by rotary evaporation to provide a viscose transparent liquid. The composition of the isolated product, 1,3-bis(2,4,6-tribromophenoxy)propan-2-yl acrylate, was confirmed by $^1$H-NMR spectroscopy.

Example 4

Synthesis of
1,3-bis(2-(phenylthio)ethylthio)propan-2-yl acrylate

Benzenethiol is reacted with 1,3-dioxolan-2-one to form 2-(phenylthio)ethanol. The 2-(phenylthio)ethanol is isolated and then converted to 2-(phenylthio)ethanethiol using triphenylphosphine, diisopropyl azodicarboxylate (DIAD), and thiolacetic acid followed by hydrolysis of the resulting acetate with potassium hydroxide in methanol.

An excess of 2-(phenylthio)ethanethiol is reacted with epichlorohydrin to form 1,3-bis(2-(phenylthio)ethylthio)propan-2-ol. In the final step, the 1,3-bis(2-(phenylthio)ethylthio)propan-2-ol is reacted with a acryloyl chloride in the presence of a tertiary alkyl amine and dimethylaminopyridine to form 1,3-bis(2-(phenylthio)ethylthio)propan-2-yl acrylate.

Example 5

Synthesis of
2-(4-chlorophenoxy)-1-[(phenylthio)methyl]ethyl
Acrylate (CPTIA)

To a 500 milliliter flask equipped with a magnetic stirrer, an addition funnel, a water-jacketed condenser and nitrogen sparge was added 250 milliliters of toluene. The flask was purged well with nitrogen and benzenethiol (14.0 ml, 0.136 mole) and 4-chlorophenyl glycidyl ether (25.0 g, 0.135 mole) were added via syringe. Tetrabutylammonium bromide (0.220 g, 6.76×10$^{-4}$ mole) was added as a catalyst. The reaction was heated to 60° C. and was allowed to stir overnight. A $^1$H-NMR revealed complete reaction of the glycidyl ether. No isolation of the product 1-(4-chlorophenoxy)-3-(phenylthio)propan-2-ol was performed.

To the flask was added triethylamine (19 mL, 0.150 mole). Acryloyl chloride (11 mL, 0.160 mole) was added dropwise as a solution in 90 mL of toluene. Once the addition was complete the reaction was brought to 60° C. for approximately two hours and then the heat was turned off. The reaction was then left to stir and cool overnight. A $^1$H-NMR revealed complete reaction of the alcohol. The amine-hydrochloride salts precipitated out of the solution and were removed by vacuum filtration through a course-fritted funnel. The solids were washed with diethyl ether. The clear yellow solution was washed with dilute aqueous hydrochloric acid three times to remove any residual amine. An additional three washes with dilute potassium hydroxide and then four washes with deionized water returned the pH to between 6 and 8. The organic layer was dried over MgSO$_4$ and filtered to remove the solids. The solvents were removed by rotary evaporation. Fifty milligrams of MEHQ were added to the flask to inhibit polymerization. No further purification was necessary. The yellowness index of CPTIA was 2.5.

Example 6

Purification of 1,3-bis(thiophenyl)propan-2-yl
acrylate (BisPTEA) to remove colored impurities The monomer 1,3-bis(thiophenyl)propan-2-yl acrylate was prepared according to a procedure similar to Example 1 using benzenethiol in place of phenol. The crude 1,3-bis(thiophenyl)propan-2-yl acrylate was purified by a variety of techniques including distillation, chromatography and by a combination of chromatography followed by distillation. A facile and convenient procedure was determined to be the dissolution of the acrylate in hexanes with stirring. A small amount of dark precipitate forms from which the hexane solution is decanted and filtered through a 4 inch (10.2 centimeters) thick pad of silica gel 3 inches (7.6 centimeters) in diameter. The silica was washed until no further product came off when analyzed by TLC. The solvent was removed by rotary evaporation with 20 mg of 4-methoxy phenol to inhibit polymerization after which a slightly turbid liquid appeared. Turbidity was removed by filtration through a 0.45 micrometer filter.

The monomer acrylates of Examples 1-3 and 5 were tested for the following properties, the results of which are provided in Table 1. Phenoxyethyl acrylate (PEA) and phenylthioethyl acrylate (PTEA) are added to the table as comparisons.

The refractive index (RI) of the acrylate monomers was measured using a Bausch and Lomb Abbe-3L refractometer; the wavelength associated with the measurement was 589.3 nanometers.

The viscosity was measured using a Brookfield LVDV-II Cone/Plate Viscometer at 25° C., with a CPE40 or CPE51 spindle attachment, 0.5 mL liquid curable composition sample volume while maintaining a torque range within 15% to 90% of the equipment maximum for the specific cone attachment. The viscosity measurements are provided in centipoise (cP).

TABLE 1

| Compound | Refractive Index | Viscosity cP | Structure |
| --- | --- | --- | --- |
| PEA | 1.518 | 10 | 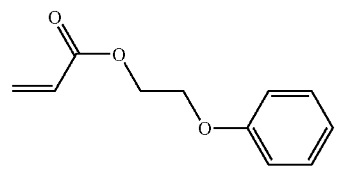 |
| PTEA | 1.557 | 9 | 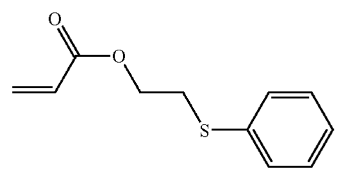 |
| Ex. 1 BisPEA | 1.551 | — | 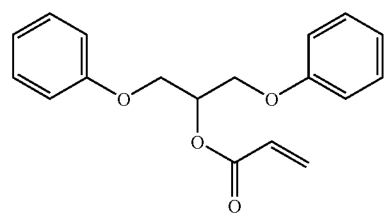 |
| Ex. 2 BisBTZA | 1.629 | 860 | 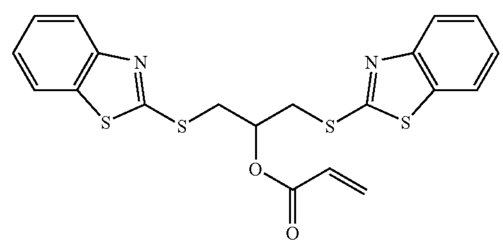 |
| Ex. 3 BisTBrPEA | 1.631 | — | 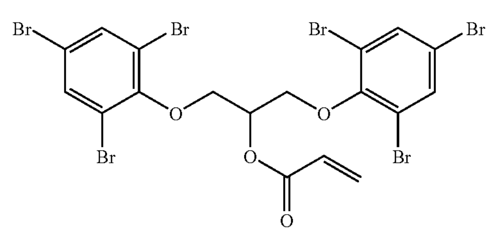 |
| Example 4 | — | — | 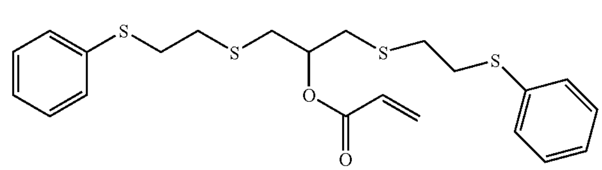 |

TABLE 1-continued

| Compound | Refractive Index | Viscosity cP | Structure |
|---|---|---|---|
| Example 5 CPTIA | 1.5792 | 352 | 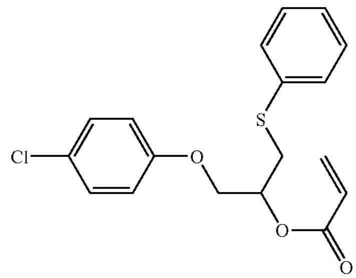 |
| Example 6 BisPTEA | 1.603 | 50 | 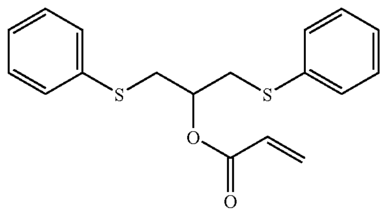 |

For the following Examples, formulations of curable compositions used to prepare cured films contain one or more of the components listed in Table 2.

TABLE 2

| Component | Trade Name | Description | Source |
|---|---|---|---|
| BisPTEA | — | 1,3-bis(thiophenyl)propan-2-yl acrylate | — |
| BisPEA | — | 1,3-bis(phenoxy)propan-2-yl acrylate | — |
| BisTBrPEA | — | 1,3-bis(2,4,6-tribromophenoxy)propan-2-yl acrylate | — |
| BisBTZA | — | 1,3-bis(2-mercaptobenzothiazoyl)propan-2-ylacrylate | — |
| CPTIA | — | 2-(4-chlorophenoxy)-1-[(phenylthio)methyl]ethyl acrylate | — |
| RDX51027 | RDX51027 | Diacrylate of tetrabromo bisphenol-A di-epoxide | UCB Chemicals |
| PTEA | BX-PTEA | 2-Phenylthioethyl acrylate | Bimax Company |
| PEA | SR339 | 2-Phenoxyethyl acrylate | Sartomer |
| Irgacure | Irgacure 819 | Bis(2,4,6-trimethylbenzoyl)-phenylphosphine oxide | Ciba-Geigy |
| Darocur | Darocur 4265 | 2-Hydroxy-2-methyl-1-phenyl-propan-1-one and Bis(2,4,6-trimethylbenzoyl)-phenylphosphine oxide | Ciba Specialty Chemicals |

Examples of cured flat films (i.e. no microstructure) were prepared according to the following procedure. As used in the Examples, coated films means a two-layered film of the composition and film substrate. Coated cured flat films having a 7 to 20 micrometer thick cured composition layer atop a 0.005-inch (0.127 centimeter) thick polycarbonate film substrate were prepared using a custom-made laminating unit and Fusion EPIC 6000UV curing system. The laminating unit consists of two rubber rolls: a bottom variable speed drive roll and a pneumatically driven top nip roll. This system is used to press together laminate stacks that are passed between the rolls. The coated flat films were prepared by transferring approximately 0.5 mL of curable composition to a highly polished, flat, chrome-plated 5 by 7-inch (12.7 by 17.8 centimeter) steel plate in a continuous line at the front, or leading edge of the plate. A piece of film substrate was then placed over the curable composition and the resulting stack sent through the laminating unit to press and distribute the curable composition uniformly between the chrome-plate and film substrate. With higher viscosity formulations, higher pressure and lower speeds were used and the chrome-plate was heated to obtain the desired thickness. Photopolymerization of the curable composition within the stack was accomplished by passing the stack under a 600-watt V-bulb at a speed of 10 feet/minute (0.051 meters/second), using high power and a focal length of 2.1 inches (5.3 centimeter), curing through the film substrate top layer. The coated cured flat film was then peeled off of the chrome-plate and used for haze, % transmission, color, yellowness index, and adhesion measurements.

Coated cured microstructured films for measuring luminance or brightness were made using a continuous coater having a coating application station and a casting station further downstream in the process from the coating station. At the coating application station, a metered amount of curable composition is applied to the base film. The curable composition can be applied either in patches or continuously. After coating, the base film proceeds to the casting station where the wet side of the film is nipped against a tool whose microstructure is a negative of the desired film microstructure. After exiting the nip, the coated film (still in contact with the microstructured tool) is exposed to ultraviolet light to cure. The base film and cured composition forming the prism film are subsequently stripped from the microstructured tool, which is reused in making the next film. The curable composition can be applied directly to the nip point in the casting station (rather than upstream); in this case, the two stations are not physically separated. The geometry of the prisms can be found in FIG. 6 of the copending U.S. application Ser. No. 10/065,981 entitled "Brightness Enhancement Film With Improved View Angle" filed Dec. 6, 2002, which is incorporated herein in its entirety.

Glass transition temperatures (Tg) of the cured compositions were measured by dynamic mechanical analysis (DMA) using a Rheometrics Solids Analyzer RSA II operating in tension with a frequency of 1.0 rad/s, strain of 0.01%, and temperature ramp of 2° C./minute. Cured free films (no film substrate) for DMA were prepared by using the same method as that described for flat films with the exception that the substrate was polyethylene. The polyethylene was the masking used to protect polycarbonate film from damage. Thus, the liquid coating was placed between the chrome plate and masked polycarbonate film with the masking side contacting the liquid. After curing a free standing film was obtained by peeling the film from the polyethylene masking.

The percent (%) haze and % transmission of light through the coated cured flat films were determined according to ASTM D1003 using a BYK-Gardner Haze-guard Plus Hazemeter.

The adhesion was measured for the coated cured flat film according to ASTM D3359.

The color of the coated cured flat films was determined by measuring L*, a*, and b* using a Gretag Macbeth Color-Eye 7000A colorimeter using L*, a*, b* color space, the D65 illuminant, and a 10 degree observer inclusive of a specular reflection.

The yellowness index (YI) of the coated cured flat films was measured using a Gretag Macbeth Color-Eye 7000A calorimeter.

The refractive index (RI) of the cured films was measured with a Metricon Corporation prism coupler Model 2010 using the thick film (bulk material) setting. The curable composition is smoothly coated onto a polycarbonate substrate and cured. The cured, smooth coating is brought into direct contact with the prism without any index matching fluid. The apparatus calculates the refractive index based on the critical angle of the prism/coating interface.

The brightness, or luminance, of the coated cured microstructured films was determined using a Microvision SS220 Display Analysis System. Microvision SS220, a computer based measurement system, uses a goniometric assembly and a mechanical positioner for the collection of in-axis and off-axis data at various locations of the films. The light source used was a LG Philips 12-inch square foot BLM (backlight module) composed of a cold cathode fluorescent lamp (CCFL) attached to the top edge of a rectangular glass panel. An aluminum bar and foam were bundled around the edges of the BLM to preserve heat around the CCFL. Five thermal couples were attached to the BLM frame and the temperature of CCFL and current to the light source were sampled every four seconds. The brightness measurements are achieved by utilizing a diffraction grating spectrometer with a collimation optical probe. The microstructured or light management film is mounted on the LG-Phillips backlight module, which is composed of a bottom diffuser D177 and a pair of crossed light management films, wherein the prism lines of the crossed light management films are perpendicular to one another. A 13-point test and hemi test are conducted to provide the uniformity of the brightness over 13 specific locations on the film and the range of viewing angle at the center location of the film. An average is taken. The brightness of backlight changes with CCFL temperature. To remove this variability of brightness once the light management film is mounted, the CCFL is allowed to reach thermal stability. All of the readings are corrected to one standard temperature, based on the linear relationship between brightness (luminance) and temperature ($L_{corrected} = L_{measured} - 6*(T_{measured} - T_{corrected})$) with the slope of 6 as the correction factor (luminance in cd/m$^2$ and temperature in ° F.). Finally, the ratio of the temperature-corrected-luminance of each sample to that of standard films is taken to provide a brightness measurement in units of candela per meter squared (cd/m$^2$).

Table 3 includes a formulation based on BisBTZA as the monomer diluent. The RI of both the liquid and the cured film are excellent, surpassing the indices of a PTEA control.

TABLE 3

| Component | Comparative Example 1 | Example 7 |
| --- | --- | --- |
| PTEA | 5.0 g. | — |
| BisBTZA | — | 2.5 g. |
| RDX51027 | 5.0 g. | 2.5 g. |
| Darocur 4265 | 0.05 g. | 0.025 g. |
| Properties | | |
| RI of Liquid | 1.5772 | 1.6205 |
| RI of cured film* | 1.6155 | 1.6475 |
| YI | 1.2 | 2.8 |
| L | 95.7 | 95.0 |
| a | −0.1 | −0.4 |
| b | 0.8 | 1.8 |

*measured with Abbe Refractometer on free film

Table 4 contains a formulation based on BisPEA as the monomer diluent. The RI of the liquid is good. Additionally, the benefit of BisPEA as opposed to a sulfur based diluent is the lack of an offensive odor.

TABLE 4

| Component | Comparative Example 2 | Example 8 |
| --- | --- | --- |
| PTEA | 2.5 g. | — |
| BisPEA | — | 2.5 g. |
| RDX51027 | 2.5 g. | 2.5 g. |
| Darocur 4265 | 0.025 g. | 0.025 g. |
| Properties | | |
| RI of Liquid | 1.5772 | 1.5721 |
| % Haze | 0.87 | 0.88 |
| % Transmission | 92.3 | 92.5 |
| YI | 1.2 | 1.9 |
| L | 95.8 | 95.7 |
| a | −0.1 | −0.2 |
| b | 0.8 | 1.2 |

Table 5 contains a formulation based on BisTBrPEA and PTEA as the monomer diluents.

TABLE 5

| Component | Example 9 |
| --- | --- |
| PTEA | 2.75 g. |
| BisTBrPEA | 2.06 g. |
| RDX51027 | 2.06 g. |
| Irgacure 819 | 0.034 g. |
| Properties | |
| % Haze | 0.86 |
| % Transmission | 92.6 |
| YI | 1.1 |
| L | 95.8 |
| a | −0.1 |
| b | 0.7 |

Table 6 illustrates a comparison of curable compositions containing PTEA, BisPTEA, or a combination of the two at varying cure conditions. The speed is in feet per minute (ft./min.; 10 ft./min.=304.8 cm/min.; 48 ft./min.=1463.04 cm/min.) and the lamp height is in inches (in.; 2 in.=5.08 cm). Again, as illustrated by Examples 10-13, the formulations containing BisPTEA provide compositions with excellent RI.

TABLE 6

| Component | C. Ex. 3 | C. Ex. 4 | Ex. 10 | Ex. 11 | Ex. 12 | Ex. 13 |
|---|---|---|---|---|---|---|
| PTEA | 5 g | 5 g | — | — | 2.5 g | 2.5 g |
| BisPTEA | — | — | 5 g | 5 g | 2.5 g | 2.5 g |
| RDX51027 | 5 g | 5 g | 5 g | 5 g | 5 g | 5 g |
| Irgacure 819 | 0.05 g | 0.05 g | 0.05 g | 0.05 g | 0.05 g | 0.05 g |
| Cure | | | | | | |
| Lamp | V | V | V | V | V | V |
| Speed (ft./min.) | 10 | 48 | 10 | 48 | 10 | 48 |
| Lamp height (in.) | 2 | 2 | 2 | 2 | 2 | 2 |
| Properties | | | | | | |
| Viscosity (cp) | 213 | 213 | 646 | 646 | 762 | 762 |
| RI liquid | 1.5740 | 1.5740 | 1.6016 | 1.6016 | 1.5937 | 1.5937 |
| Haze (%) | 1.04 | 0.96 | 1.20 | 1.32* | 1.24 | 1.02 |
| Transmission (%) | 92.6 | 92.6 | 92.0 | 91.9* | 92.4 | 92.2 |
| Color (YI) | 0.5 | 0.4 | 1.3 | 0.9* | 0.8 | 0.7 |
| Adhesion | 5 B | 5 B | 0 B | 0 B | 5 B | 4 B |

*Properties were measured on the free film

Examples 14 and 15 are directed to coated cured microstructured films prepared from compositions containing the high refractive index monomer BisPTEA. As illustrated in the results found in Table 7, the composition containing BisPTEA exhibits a higher refractive index when compared to compositions containing PTEA. Furthermore, when cured into microstructured films, the BisPTEA compositions provide improved brightness in comparison to the PTEA-based materials. Table 7.

TABLE 7

| Component | C. Ex. 5 | Ex. 14 | Ex. 15 |
|---|---|---|---|
| PTEA (wt. %) | 49.50 | — | 24.75 |
| BisPTEA (wt. %) | — | 49.50 | 24.76 |
| RDX51027 (wt. %) | 50.00 | 50.00 | 50.00 |
| Irgacure 819 (wt. %) | 0.50 | 0.50 | 0.50 |
| Properties | | | |
| Viscosity @ 25° C. (cP) | 213 | — | 762 |
| Viscosity @ 50° C. (cP) | — | 646 | — |
| RI Liquid | 1.5740 | 1.6016 | 1.5937 |
| Haze (%) | 1.04 | 1.20 | 1.24 |

TABLE 7-continued

| Component | C. Ex. 5 | Ex. 14 | Ex. 15 |
|---|---|---|---|
| Transmission (%) | 92.6 | 92.0 | 92.4 |
| YI | 0.5 | 1.3 | 0.8 |
| Adhesion | 5B | 0B | 5B |
| Tg @ 10 ft./min. lamp height 2 in. (° C.) | 49 | 53 | 52 |
| Tg @ 48 ft./min. lamp height 2 in. (° C.) | 40 | 48 | 40 |
| Brightness (cd/m$^2$) | 863.7 | — | 880.8 |

Table 8 provides the results of coated cured flat films comprising CPTIA as a high refractive index monomer. As illustrated by the results, compositions containing CPTIA exhibited excellent RI as compared to compositions containing only PEA or PTEA as the monomer. CPTIA also provided a composition with good RI even when blended with another monomer as shown in Examples 17-18.

TABLE 8

| Component | C. Ex. 6 | C. Ex. 7 | Ex. 16 | Ex. 17 | Ex. 18 |
|---|---|---|---|---|---|
| PTEA (wt. %) | 49.5 | — | — | 24.75 | 37.12 |
| PEA (wt. %) | — | 49.5 | — | — | — |
| CPTIA (wt. %) | — | — | 49.5 | 24.75 | 12.38 |
| RDX51027 (wt. %) | 50.0 | 50.0 | 50.0 | 50.0 | 50.0 |
| Irgacure 819 (wt. %) | 0.5 | 0.5 | 0.5 | 0.5 | 0.5 |
| Cure | | | | | |
| Lamp | V | V | V | V | V |
| Speed (ft./min.) | 10 | 10 | 10 | 10 | 10 |
| Lamp height (in.) | 2 | 2 | 2 | 2 | 2 |
| Properties | | | | | |
| RI Liquid | 1.5741 | 1.5486 | 1.5887 | 1.5816 | 1.5781 |
| Viscosity (cP) | 183 | 333 | 24,024 | 1213 | 473 |
| Haze (%) | 0.71 | 0.71 | 1.33* | 0.89 | 0.79 |
| Transmission (%) | 92.7 | 93.0 | 92.3* | 92.6 | 92.7 |
| YI | 0.6 | 0.5 | 1.4* | 0.7 | 0.6 |

TABLE 8-continued

| Component | C. Ex. 6 | C. Ex. 7 | Ex. 16 | Ex. 17 | Ex. 18 |
|---|---|---|---|---|---|
| Adhesion | 5 B | 5 B | 0 B | 5 B | 5 B |
| Tg | 41 | 47 | 62 | 48.5 | 43 |

*Measurements made on a free standing film

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A high refractive index monomer, comprising:
a compound according to formula (I)

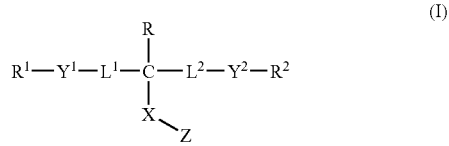

(I)

wherein Z is an ethylenically unsaturated group;
X is O, S, or NH;
$L^1$ and $L^2$ are each independently $C_1$-$C_3$ alkylene, —($C_1$-$C_3$ alkylene)-S—($C_1$-$C_3$ alkylene)-, or —($C_1$-$C_3$ alkylene)-O—($C_1$-$C_3$ alkylene)-;
R is hydrogen or $C_1$-$C_6$ alkyl;
$R^1$ and $R^2$ are each independently N-containing heteroaryl, or N-containing heteroaryl($C_1$-$C_6$ alkylene)-, each of which group is substituted with 0 to 5 substituents independently chosen from halogen, $C_1$-$C_4$alkyl, $C_1$-$C_4$alkoxy, ($C_1$-$C_4$alkyl)S—, $C_1$-$C_4$haloalkyl, and $C_1$-$C_4$haloalkoxy; and
$Y^1$ and $Y^2$ are each independently O, S, NH.

2. The monomer of claim 1, wherein Z is acryloyl, methacryloyl, vinyl, or allyl; X is O or S; and R is hydrogen.

3. The monomer of claim 1, wherein $L^1$ and $L^2$ are each independently methylene; ethylene; —($C_1$ alkylene)-S—($C_2$ alkylene)-, or —($C_2$ alkylene)-S—($C_1$ alkylene)-; —($C_1$ alkylene)-O—($C_2$ alkylene)-, or —($C_2$ alkylene)-O—($C_1$ alkylene)-.

4. The monomer of claim 1, wherein $R^1$ and $R^2$ are each independently benzo[d]thiazolyl, benzo[d]oxazolyl, benzofuranyl, benzothiophenyl, benzoxadiazolyl, imidazolyl, indolyl, isoxazolyl, oxazolyl, N-phenothiazinyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, or triazolyl.

5. The monomer of claim 4, wherein $Y^1$ and $Y^2$ are S.

6. The monomer of claim 1, wherein the compound is 1,3-bis(benzo[d]thiazol-2-ylthio)propan-2-yl acrylate; 1,3-di(10H-phenothiazin-10-yl)propan-2-yl acrylate.

7. A high refractive index monomer comprising:
a compound according to formula (VI)

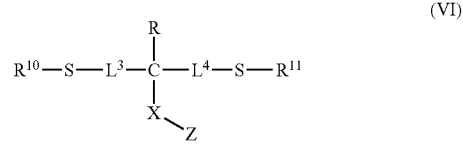

(VI)

wherein Z is an ethylenicaily unsaturated group; X is O, S, or NH;
L3 and L4 are each independently
—($C_1$-$C_3$ alkylene)-S—($C_1$-$C_3$ alkylene)-,
or
—($C_1$-$C_3$ alkylene)-O—($C_1$-$C_3$ alkylene)-;
R is hydrogen or C1-C6 alkyl;
R10 and R11 are each independently aryl, including phenyl or naphthyl, aryl (C1-C6 alkylene)-; heteroaryl, or heteroaryl (C1-C6 alkylene)-; each or which group is substituted with 0 to 5 substituents independently chosen from halogen, C1-C4 alkyl, C1-C4 alkoxy, (C1-C4 alkyl)-S—, C1-C4 haloalkyl, and C1-C4 haloalkoxy.

8. The monomer of claim 7, wherein Z is acryloxy, methacryloxy, vinyl or allyl; X is O or S; and R is hydrogen.

9. The monomer of ciaim 7, wherein L3 and L4 are each independently —(—$C_1$ alkylene)-S—($C_2$ alkylene)-; —($C_2$ alkylene)-S—($C_1$ alkylene); —($C_1$ alkylene)-O—($C_2$ alkylene)-; or ($C_2$ alkylene)-O—($C_1$ alkylene)-.

10. The monomer of claim 7, wherein $R^{10}$ and $R^{11}$ are each independently phenyl, 3-bromophenyl, 4-bromophenyl, 2,4,6-tribromophenyl, naphthyl, benzo[d]thiazolyl, benzo[d]oxazolyl, benzofuranyl, benzothiophenyl, benzooxadiazolyl, dihydrobenzodioxynyl, furanyl, imidazolyl, indolyl, isoxazolyl, oxazolyl, N-phenothiazinyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, or triazolyl.

11. The monomer of claim 7, wherein the compound is 1,3-bis(2-phenylthio)ethylthio)propan-2-yl acrylate.

* * * * *